United States Patent
Cianciotta

(10) Patent No.: US 7,637,881 B2
(45) Date of Patent: Dec. 29, 2009

(54) FRAGRANCED CAST APPLICANT AND METHOD OF APPLICATION

(76) Inventor: Saverio Cianciotta, 4 River St., Lindenhurst, NY (US) 11757

( * ) Notice: Subject to any disclaimer, the term of this patent is extended or adjusted under 35 U.S.C. 154(b) by 235 days.

(21) Appl. No.: 11/706,564

(22) Filed: Feb. 15, 2007

(65) Prior Publication Data

US 2007/0208287 A1    Sep. 6, 2007

Related U.S. Application Data

(60) Provisional application No. 60/775,040, filed on Feb. 17, 2006.

(51) Int. Cl.
*A61F 5/00* (2006.01)
(52) U.S. Cl. ............................................. 602/5; 602/8
(58) Field of Classification Search ................ 602/5–8, 602/13
See application file for complete search history.

(56) References Cited

U.S. PATENT DOCUMENTS

| 5,997,492 | A  | * | 12/1999 | Delmore et al. | 602/8 |
| 6,458,751 | B1 | * | 10/2002 | Abbas et al. | 510/141 |
| 2004/0068920 | A1 | * | 4/2004 | Steele et al. | 44/275 |
| 2006/0246020 | A1 | * | 11/2006 | Cole et al. | 424/59 |

* cited by examiner

*Primary Examiner*—Michael A. Brown
(74) *Attorney, Agent, or Firm*—Thomas A. O'Rourke; Bodner & O'Rourke, LLP

(57) ABSTRACT

An article useful in orthopedic cast care is described as well as a method of making the article and applying it to the cast. The article is a fragranced solid or semi-solid material that is applied to an orthopedic cast by rubbing it over the outside so as to reduce or mask the unpleasant odor resulting from sweat and dirt building up inside the cast and to provide a pleasant fragrance.

10 Claims, No Drawings

FRAGRANCED CAST APPLICANT AND METHOD OF APPLICATION

The present application claims priority on U.S. Provisional Patent Application Ser. No. 60/775,040 filed on Feb. 17, 2006, the disclosures of which are incorporated herein by reference.

FIELD OF THE INVENTION

The present invention relates generally to the field of orthopedic cast care, and more particularly to a fragranced solid or semi-solid material for application on orthopedic casts and the method of applying the applicant to an orthopedic cast by rubbing it over the outside so as to reduce or mask the unpleasant odor resulting from sweat and dirt building up inside the cast and to provide a pleasant fragrance.

BACKGROUND OF THE INVENTION

I. Description of Prior Art

Recorded fracture treatment dates back to 3000 B.C. when crude splints were constructed from bark and palm ribs and held together by gum, egg whites, goat's wool, clay and plaster. Since then, technology has progressed in the medical care for fractured bones. Nowadays, orthopedic surgeons commonly use casts to support and protect injured bones. While casts are uncomfortable and burdensome, they are a successful and efficient method to treat broken bones and have been the common treatment for a number of years. Casts come in many shapes and sizes, but the two most common types are plaster and fiberglass. The preference for these two cast types stems from their ability to be custom-fit for the patient. For less severe injuries, sometimes a removable splint will be custom-made for the patient out of the same or similar materials or can be purchased without personal tailoring in many shapes and sizes.

Plaster is the older material used for setting casts and its use dates back to the mid-19$^{th}$ century, when Parisian developers first used the material, then called "Plaster of Paris" to create crude casts for treatment of broken bones. Plaster is a material based on calcium sulfate hemihydrate and is created by heating gypsum to about 150° C. A plaster cast is usually applied immediately after the injury occurs in order to allow the bone to heal properly. Plaster is applied to the patient's broken body part while the material is wet. Cotton and ace bandages are placed in between the patient's skin and the wet plaster in order to lessen the lack of comfort when the plaster hardens. The reason plaster is applied while wet is that a chemical reaction occurs between the water and the calcium sulfate, which produces heat and causes the cast to harden or set around the patient's broken appendage in the shape in which the bone is set. A patient can typically begin to feel the plaster cast harden within 10-15 minutes of its application. Nevertheless it will take 24-48 hours to fully set. Problems with the plaster cast are numerous, and include but are not limited to, the heaviness and bulkiness of the plaster material and the fact that it must remain dry at all times because it will re-set if moistened. This leads to many bathing inconveniences for patients.

With the development of synthetic materials, the fiberglass cast became a lightweight alternative to plaster in the 1970s. Today, 75 percent of all casts in the United States are made of synthetic materials. Fiberglass-based cast materials typically come in two structural forms. The basic form involves a roll of tape anywhere from one to five inches wide that is applied by wrapping the tape around the limb to be cast. A second general structural form involves a pre-cut sheet of the material sized and shaped to fit around a specific appendage such as a wrist and forearm or an ankle and foot. The latter configuration is typically easier to apply but less conformable to the variety of sizes and shapes of limbs. The former structure (tape) is more versatile but is generally more difficult to apply. Fiberglass tape is applied in a similar fashion to the plaster cast, as it is also wet when rolled onto the injured body part, allowing time to harden and dry. Fiberglass casts, however, are not usually fitted until swelling has subsided. As a result, a splint made out of plaster, which allows room for swelling, is often placed on a patient for the first week after a bone is broken. Then, the patient will return to the doctor and have a fiberglass cast put on for the remainder of the healing time. While solving the problem of the bulkiness of the plaster cast, a fiberglass cast too cannot be moistened and must be kept dry at all times.

The ancillary effect of the necessity in keeping these casts dry at all times as well as the byproduct of the casts themselves is another major complaint of patients treated for broken bones. This effect is an unpleasant odor emanating from the injured body part now consumed by a plaster or fiberglass cast. This odor is a byproduct of the combination of not being able to properly clean the area of the body covered in the cast and the ensuing buildup of sweat and dirt in between the cast and the skin. The fiberglass casts compound this problem due to their odor and because they also leave behind residue and dust on the skin which smell and can lead to skin irritation and rashes. The cleaning methods previously available and advised by physicians to reduce this uncomfortable effect of broken bone treatment have included wiping a fiberglass cast with a moistened cloth and immediately drying with a hairdryer, as well as wiping a plaster cast with a dry cloth, and have proven tedious and ineffective at reducing the odor.

One recent invention has sought a solution to this problem through making fiberglass casts "waterproof." The PRO-CEL® Cast Liner, a product of W. L. Gore & Associates, uses innovation from U.S. Pat. No. 6,942,628 issued to Richard L. Watson on Sep. 13, 2005. The objective of this inventor was to provide a waterproof cast liner, which would allow patients wearing a fiberglass cast to bath, shower or even swim. This objective was achieved through the formation of a sheet-like element made of a fiberglass and solidifying resin-based orthopedic casting material made from layers of resin impregnated fiberglass fibers that are shaped, cut, or otherwise formed into a skeletal hexagonal cellular mesh array. The sheet-like element has an arrangement of apertures through which the flow of air is permitted through and beads of water are filtered through. The result has been the ability for this cast liner to drain out water from the cast, preventing the unwanted side effects of mildew and mold forming from trapped water in the fiberglass cast, as well as the ability of a patient wearing this invention to bathe and thereby avoid the buildup of dirt and sweat.

U.S. Pat. No. 6,974,430, issued to John C. Evans on Dec. 13, 2005, entitled KNITTED SUBSTRATE WITH HIGH AND LOW TENACITY YARNS FOR USE IN BANDAGING PRODUCT, BANDAGING PRODUCT AND METHOD OF FORMING THE SAME, describes a cast tape or medical bandaging product formed from a resin-coated or impregnated fabric material that includes a knitted substrate having a combination of non-fiberglass high and low tenacity yarns such as polypropylene, polyester and elastomer. The polypropylene and polyester yarns have a high number of filaments, typically 48 to 90 filaments. This new substrate does not disintegrate into irritating dust and/or fibers when removed from the injured body part of a patient, and thus purports to eliminate the odor and irritation associated with fiberglass casts.

U.S. Pat. No. 5,527,265, issued to William H. McKeel on Jun. 18, 1996, entitled ORTHOPEDIC AIRFLOW CAST PAD AND METHOD, describes a base pad with a plurality of cushions projecting outward in a particular pattern to create a collection of air channels that can be molded or formed from a single sheet of a water impermeable material, such as a thermal closed cell polyethylene. The pad allows airflow to the skin through the air channels to minimize rashes and itching under the cast and to eliminate odor collection and reduce moisture against the skin.

U.S. Pat. No. 5,540,964, issued to Ted A. Mallen on Sep. 14, 1994, entitled MOISTURE TRANSFER CASTLINING MATERIAL FOR USE BENEATH AN ORTHOPEDIC CAST, BEING IN THE FORM OF A FABRIC AND CONSISTING ESSENTIALLY OF SYNTHETIC HYDROPHOBIC FIBERS . . . , describes a cast lining material prepared from a moisture transporting synthetic fiber fabric which transports moisture from the skin and environment beneath a cast or other orthopedic device to the outside environment where the moisture is removed by evaporation providing a dry atmosphere beneath the cast. The resulting dry environment reduces the ill effects of bacterial, fungal and mildew growth, reduces odor, increases dryness and comfort, and allows the wearer to bathe and swim.

U.S. Pat. No. 5,098,693, issued to Faas, Jr., et al. on Mar. 24, 1992, entitled ANTI-IRRITANT SPRAY FOR USE WITH CAST AND METHOD OF APPLICATION, describes an anti-irritant, anti-moisture mixture that is applied via an aerosol spray composed of any readily available and known fluorocarbon propellant, one suitable propellant mixture being hydrochlorofluorocarbon 22 and dimethylether. The "anti-itch" spray provides a soothing sensation over the cast area and the talc acts to absorb any existing moisture. The aerosol propellants and the spray carriers evaporate as a result of the heat generated from the person's body. This leaves the talc and triclosan deposited on the skin to absorb any additional moisture as it is formed, as well as inhibit the formation of any odor resulting from the cast.

Although a number of the materials, methods and compositions described above purport to produce a solution to the problem of the unpleasant smell resulting from the shortcomings of current plaster and fiberglass casts, a problem which has persisted is the inability to "improve" the scent of the area in a cast because liquid or vapor fragrances will likely produce mildew or mold under the cast and may irritate the skin. The present invention provides a solution to the problem of unpleasant odor while providing a pleasant scent and not risking the mildew, mold, or skin irritation that would result from a liquid applicant. Furthermore, none of the above patents has proposed a scented deodorant, which could be applied to the surface of the cast to fragrance it and eliminate the odor.

II. Objects of the Invention

It is therefore an object of the present invention to provide a scented material for use in the care and maintenance of orthopedic casts, which will be compact and easily portable to the user.

It is another object of the present invention to provide a scented material for use in the care and maintenance of orthopedic casts that is solid or semi-solid and thus will not deteriorate or harm the plaster or fiberglass material of the orthopedic cast.

It is a further object of the present invention to provide a scented material for use in the care and maintenance of orthopedic casts that reduces or even eliminates the unpleasant odor that results from sweat, dirt, dead skin, and dust buildup in the area between the cast material and the skin.

It is further object of the present invention to provide a scented material for use in the care and maintenance of orthopedic casts that provides a pleasant fragrance upon application to the cast and the body part of the patient that wears the cast.

It is a further object of the present invention to provide a scented material for use in the care and maintenance of orthopedic casts that provides a pleasing aesthetic appeal to children and others so interested.

It is a further object of the present invention to provide a scented material for use in the care and maintenance of orthopedic casts that will enable the patient wearing the orthopedic cast to eliminate unpleasant odor and create a pleasant fragrance over the cast without necessitating further visits to the doctor once the cast has already been fitted.

It is a further object of the present invention to provide a scented material for use in the care and maintenance of orthopedic casts that is hydrophobic and thus will not wash off the cast.

It is a further object of the present invention to provide a scented material for the use in the care and maintenance of orthopedic casts that will enable the patient to eliminate the unpleasant odor, creating a pleasant fragrance without coming into direct contact, irritating or harming the patient's skin.

SUMMARY OF THE INVENTION

The present invention is directed to an improved method of treating an orthopedic cast on a patient. Patients who have had casts placed over broken bones, torn ligaments and the like frequently have to wear the cast for many days or weeks. These casts can cause a buildup of odors from sweat, dirt and moisture. While the cast in rare instances could be removed and cleaned, in most situations it is usually not medically advisable to remove the cast except in limited circumstances and even then it has to be supervised by a physician. In order to eliminate the odor buildup in connection with these casts, an improved deodorant system has been developed. This system is made up of a spreadable solid or semi-solid hydrophobic base material that does not support the growth of bacteria. The hydrophobic base material is combined with a fragrance. The hydrophobic material is preferably a spreadable material that does not readily dissolve in water. One preferred material is a wax which may be a petroleum based wax or other type of wax such as a plant or animal based wax. To the wax is added a fragrance which can be any one or more materials to provide a pleasing odor to mask the smell of the cast. The composition may be in a solid or semi-solid form and in a variety of shapes as desired. The composition may be applied by means of friction, i.e. by rubbing the solid or semi-solid spreadable material on to an outer surface of the cast. By the term spreadable is meant that friction of the hydrophobic material against the cast causes the hydrophobic material to be deposited along with the fragrance blended therein onto the outer surface of the cast material. Although a solid or semi-solid material containing a fragrance is preferably used, a liquid form of the composition may be painted onto the cast by brushing, dripping or other suitable means.

The preferred composition of the present invention may be formed by heating the spreadable hydrophobic material until it is in a plastic or liquid condition. One or more fragrances may be added to the hydrophobic material to provide a masking agent for the unpleasant odors emanating from a cast. The blend of the hydrophobic material and the fragrance may be blended by any suitable means to cause the fragrance to be contained throughout the hydrophobic material. The composition may then be cooled so that the composition hardens into a mass that may be spread by friction onto the cast.

One or more hardeners can be added to the composition to facilitate hardening of the composition. The fragrance can include any number of natural or artificial fragrances that may be blended in the composition. The blend may be formed in any suitable container, however, it has been found that a double boiler type arrangement may be used to avoid burning the hydrophobic material as it is heated. In the double boiler arrangement, a fluid such as water is placed in a first receptacle. The first receptacle is the one that is closest to a heat source. The hydrophobic material may be placed in the second receptacle which is above the first receptacle and further from the heat. The fluid in the first receptacle preferably has a boiling point less than the flashpoint of the hydrophobic material.

DETAILED DESCRIPTION OF THE INVENTION

The present invention is a spreadable material of solid or semi-solid form which can be used to fragrance the outside of an orthopedic cast and eliminate or at least hide or reduce the unpleasant odor associated with the extended wearing of an orthopedic cast as a means of treating a fractured bone or other injury. Although paraffin wax is the preferred material employed in this embodiment of the present invention, the innovation here is not limited to this material alone. There are various other solid and semi-solid hydrophobic materials, taken alone or as blends, such as resins, gums and other waxes such as natural or hydrocarbon based waxes, which make up the hydrophobic material herein described.

Other suitable hydrophobic solid and semi-solid materials include but are not limited to beeswax, soy wax, candle wax such as bay berry candle wax, gel wax, jelly candle wax, starburst wax, micro-crystalline wax and the like.

In addition to waxes, other possible materials include materials known as wax hardeners including but not limited to Paraflent H-1, MicroWax 175, MicroWax 195, Poly AC-6A, Poly AC-400, Stearic powder, Visbar 103, Vybar 260 and the like.

For example, a hydrophobic composition in the form of many typical soft-solid deodorants could easily be applied to this type of invention. These products are typically made up of a clay thickening agent and an activator for the clay, particulate thickening agents, selected volatile and/or non-volatile alkylmethylsiloxanes, or triglyceride gallants. Another embodiment could provide a gum composition much like the hydrophobic gum like the guar gum used in washing and conditioning the hair and skin, in U.S. Pat. No. 6,387,855, issued to Roland De La Mettrie on May 14, 2002. The main requirement is that the solid or semi-solid material in any embodiment of the present invention be hydrophobic so that it will not wash off if water comes into contact with the cast.

Furthermore, although a bar is listed as the present description of the form of the wax applicant, several forms can easily be attributed to this. In fact, in solid form, the material may be molded to form an animal or other shape that children enjoy. Furthermore, it would only be fitting that a deodorant such as this could also be found in stick form much like deodorant. An applicator like that used for cosmetics (lipstick or lip gloss) could also be used to apply the fragranced solid. In another embodiment of this invention, a liquid or pasty semi-solid form of the scented material herein described could be spread on the cast via a brush. A further possible embodiment would be a jarred solid in gel or jelly form that could be smeared on the cast like a lip balm would be applied. Finally, another possible embodiment is a spreadable semi-solid in a dispenser much like that used for lotions or anti-bacterial soaps. While the above possible variations would seem the more commonplace adaptations on the present invention, they are not exhaustive and are merely exemplary of the many various embodiments possible to come out of the present invention. This is even more significant since the composition of the present embodiment is paraffin wax, which can be molded into an infinite number of different forms.

The present invention further involves the method of developing and applying the wax to orthopedic casts. The fragranced solid or semi-solid deodorant herein described can be used in association with plaster or synthetic fiberglass orthopedic casts, but is not limited to conformity with those types of casts. The method of application also could be applied any other form of encasing of the body for a period of time which may or may not result in unpleasant odor or buildup of sweat and dirt typically associated with the wearing of an orthopedic cast. Alternate materials for casts do include thermoplastic resins, which can be formed at a temperature higher than room temperature, but not at temperatures that are uncomfortable for the patient of the person applying the cast. This method of application could be applicable to these forms of casts as well.

The method of production of the solid abrasive is important to an understanding of the widespread possible applications of the invention itself. In producing the composition of the present invention, a hydrophobic spreadable solid or semi solid material is heated to below its flashpoint. Once the material has been melted, the fragrance may be added. The fragrance is preferably a liquid fragrance, although a solid may be added provided its melting point is the same as or lower than the temperature of the melted hydrophobic material. A hardener may also be added to the mixture. The composition is mixed so that the fragrance extends throughout the composition. The material can then be cooled to its hardening point. In a preferred embodiment, the composition may be cooled in a mold.

In a specific embodiment, paraffin wax (candle wax) of the type sold in most supermarkets is heated in a double boiler. The heating is done in the double boiler because heating wax directly over a flame will result in the wax itself being burned. A double boiler is the efficient and, in reality, only recommended means for melting wax because the temperature can be somewhat controlled by the wax being in water. The flashpoint of wax is typically over 300° F. Thus, heating in a double boiler provides sufficient heat to melt the wax (the heat in a properly supervised double boiler never exceeds 212° F.) without letting it exceed its flashpoint and scorching or possibly starting a fire.

Boiling a receptacle containing water on a heat source is the first step to creating a double boiler. The pouring pot (containing the wax) is then placed within this boiling water. In essence, the pouring pot is never in direct contact with the heat source. The boiling water transmits the heat to the pouring pot quickly and evenly, without scorching the wax and minimizes the chances of a fire. To begin, about an inch or two of water is poured into the boiling pot and brought to a boil. The pouring pot is then placed into the boiling pot and the heat is lowered to a simmer. This leaves the temperature at 212° F., well below the flashpoint of the paraffin wax. Periodically, water must be added to replace the evaporating water in the boiling pot because, if the boiling pot runs dry, the wax will quickly burn.

To the 1-lb. of melted wax in the double boiler, a fragrance is added. In one embodiment, 1/16 fl. oz. of liquid fragrance may be added to the melted wax before a mold is used. The fragrance may be added for example by an eye dropper. A hardener may also be added as well to the fragrance wax mixture. In another embodiment, the fragrance may be added afterwards. However, since the flashpoint of most liquid fragrances are lower than that of the paraffin wax or other solid, and some are even below 170° F., the first embodiment is the preferred one. The key component of most fragrances are essential oils, which are concentrated, hydrophobic liquids containing volatile aromatic compounds extracted usually from natural sources, namely plants. They are typically produced through distillation and are the sources of natural fragrances, which are used in various aromatherapy techniques. Examples of essential oils are Basil leaf, black pepper, ginger rhizome, lavender, rose, peppermint, thyme, etc. These natural fragrances could be applied to the solid or semi-solid material in one embodiment. In another embodiment, essential oils, combined with other aromatic compounds that are synthetically-produced could be used to create a unique perfume. In a further embodiment, no essential oils could be used at all and the entire fragrance could be formed from a synthetic aroma compound. In either of these latter two embodiments, if these aroma compounds are combined with a carrier like propylene glycol, mineral oil or vegetable oil, the result is fragrance oil. Fragrance oils are used in the creation of many perfumes and other fragrances. Some examples of synthetic fragrances, which have been applied in the present invention or could be applied in the future are the scents that can be applied are Apple, Blueberry Cheesecake, Cinnamon, French Vanilla, Peaches and Cream, Pina Colada, etc. Typically, the essential oils have much lower flashpoints (many around 100-120° F.) than the fragrance oils and, therefore, they must be added at a lower temperature than the less volatile fragrance oils. In another embodiment, solid fragrances, such as potpourri could be applied to the solid or semi-solid material being molded. Basically, any suitable fragrance can be used, combining natural and synthetic aroma compounds, depending on the patient's taste, so that all elements of the cast will be "custom-fit."

A final additive to the mixture is Polyboost™ 165, a polymer manufactured by S&S Chemical, LLC that binds the oil in paraffins and disperses colorants and fragrances into the paraffin phase. Because its flashpoint is greater than 350° F. it is no threat to burn at these temperatures. It has basically the same melt point, viscosity, and cloud point as the paraffin wax and is manufactured specifically to take the vibrance of the wax's color and aroma of its fragrance to new heights. S&S Chemical, LLC, POLYBOOST 165 data sheet <http://www.snschemical.com/POLYBOOST%20165%20data%20sheet.htm> (accessed Feb. 16, 2006).

Polyboost™ 165 is intended to be a substitute in candle-making for the VYBAR® Polymers, and in another embodiment a VYBAR® polymer could be added in the place of the Polyboost™ either in whole or partially. VYBAR® Polymers are manufactured by Baker Petrolite Polymers Division (BPPD), and are low molecular weight, poly-alpha-olefins, which are intended to provide solutions to the typical candle problems and improve overall candle performance. Because, in the present embodiment, paraffin wax is used, these same benefits can be realized in the production of the present invention. Benefits include improved surface appearance, uniform dye dispersion, higher fragrance loads leading to improvement in opacity, flow, hardness, strength, dispersion of color and retention of fragrance. The hyperbranched polymer configuration of VYBAR® 103 and 260 polymers allows these polymers to alter the crystallization process of paraffinic materials, resulting in hardening fully refined paraffins (FRPs) and binding oil and low molecular fractions in high oil content paraffins/slack waxes. Thus, when added at concentrations as low as 0.5% by weight, they can achieve the aimed improvements to the wax compound typically without altering the viscosity and cloud point of the blend.

VYBAR® Polymers and Polyboost™ Polymers are also both intended to be partial or total substitutes for stearic acid in candle making. Therefore, an embodiment in which stearic acid and stearin replace, totally or in part, the polymers described above could easily be envisioned. Stearic acid is a saturated fatty acid that comes from many animal and vegetable fats and oils. It is a waxy solid of chemical formula $CH_3(CH_2)_{16}COOH$ and is used in candle making to harden and opacify wax. Stearin, the glyceryl ester of stearic acid, is also used as tallow in the manufacture of candles, and creates stronger candles.

Once the wax is melted and the fragrance and the hardener/binder are added, the wax is molded into the shape of the solid or semi-solid; whether it is a bar, stick, paste, lotion or even circus animal could also be based on the patient's tastes. At this point the wax form can be either frozen to speed up the solidification process or it can be hardened more gradually at room temperature.

Once hardened, the bar, stick or other form of fragranced wax is ready for application. Application is made upon the hardened orthopedic cast of the patient by rubbing the wax along the length of the cast. Sparkles or glitter may be applied to the bar as well so that it produces a sparkling glow on the patient's cast. After the abrasive is applied to the cast, it is given to the patient to take home and apply themselves without requiring any further visits to the doctor for cast care or maintenance because of unpleasant odor problems resulting from sweat, dirt, dead skin or dust buildup in the area in between the cast and the patient's skin.

What is claimed is:

1. A method of treated an orthopedic cast on a patient comprising
applying to a surface of the cast a spreadable composition comprising solid of semi solid hydrophobic material, said material containing a fragrance, said composition being formed by melting said hydrophobic material to a temperature below its flashpoint, adding a fragrance to the melted hydrophobic material, blending said composition and cooling said composition in a mold.

2. The method according to claim 1 wherein said material is spread over a portion of said cast.

3. The method according to claim 1 wherein the solid or semi solid material comprises a wax.

4. The method according to claim 3 wherein the wax is a paraffin wax.

5. The method according to claim 1 wherein the solid of semi solid material comprises a wax hardener.

6. The method according to claim 1 wherein said solid or semi solid material comprises a gum.

7. The method according to claim 1 wherein said solid or semi solid material comprises a triglyceride.

8. The method according to claim 1 wherein said hydrophobic material is heated in an apparatus having a first receptacle and a second receptacle, said first receptacle being in closer proximity to a heat source than said second receptacle, said first receptacle containing a fluid with a boiling point lower than the flashpoint of the hydrophobic material, said second receptacle containing said hydrophobic material that is melted by said heat source.

9. The method according to claim 8 wherein a hardener is added to the melted blend of hydrophobic material and fragrance.

10. The method according to claim 9 wherein said hardener has a flashpoint greater than the flashpoint of said hydrophobic material.

* * * * *